(12) United States Patent
Mulrooney

(10) Patent No.: US 12,220,545 B2
(45) Date of Patent: Feb. 11, 2025

(54) GARMENT CLIP

(71) Applicant: Phagenesis Limited, Manchester (GB)

(72) Inventor: Conor Mulrooney, Manchester (GB)

(73) Assignee: Phagenesis Limited, Manchester (GB)

( * ) Notice: Subject to any disclaimer, the term of this patent is extended or adjusted under 35 U.S.C. 154(b) by 0 days.

(21) Appl. No.: 17/247,182

(22) Filed: Dec. 2, 2020

(65) Prior Publication Data

US 2021/0077784 A1   Mar. 18, 2021

Related U.S. Application Data

(63) Continuation of application No. 15/749,944, filed as application No. PCT/GB2016/052381 on Aug. 3, 2016, now Pat. No. 10,888,690.

(30) Foreign Application Priority Data

Aug. 4, 2015 (GB) .................................... 1513792

(51) Int. Cl.
| | | |
|---|---|---|
| *A61M 25/02* | (2006.01) | |
| *F16L 3/237* | (2006.01) | |
| *H04R 1/10* | (2006.01) | |

(52) U.S. Cl.
CPC ....... *A61M 25/02* (2013.01); *A61M 2025/024* (2013.01); *A61M 2025/028* (2013.01); *F16L 3/237* (2013.01); *H04R 1/1033* (2013.01); *Y10T 24/13* (2015.01); *Y10T 24/3444* (2015.01)

(58) Field of Classification Search
CPC ............ A61M 25/02; A61M 2025/024; A61M 2025/028; A61M 5/1418; A61M 39/10; H04R 1/1033; F16L 3/223; F16L 3/237; Y10T 24/1391; Y10T 24/3444; Y10T 24/1394; Y10T 24/1365
See application file for complete search history.

(56) References Cited

U.S. PATENT DOCUMENTS

| | | | | |
|---|---|---|---|---|
| 803,464 | A | * 10/1905 | Beck | ........................ F16L 3/237 24/339 |
| 1,032,436 | A | * 7/1912 | Smith | ................... B43K 23/001 24/11 CT |
| 2,592,506 | A | 4/1952 | Thomas | |

(Continued)

FOREIGN PATENT DOCUMENTS

| | | |
|---|---|---|
| CN | 203389196 U | 1/2014 |
| CN | 203954394 U | 11/2014 |

(Continued)

OTHER PUBLICATIONS

Fraser, Chris et al., Driving Plasticity in Human Adult Motor Cortex is Associated with Improved Motor Function After Brian Injury, Neuron, vol. 34, 831-840, May 30, 2002.

(Continued)

*Primary Examiner* — Robert Sandy
*Assistant Examiner* — Rowland Do
(74) *Attorney, Agent, or Firm* — Fortem IP LLP

(57) ABSTRACT

A clip for attaching a flexible cable or tube to clothing. The clip comprises a body and a clasp for attaching the body of the clip to clothing. The body comprises at least one receiving formation in the form of a resiliently deformable channel for receiving a flexible cable or tube.

14 Claims, 2 Drawing Sheets

(56) References Cited

U.S. PATENT DOCUMENTS

| | | | | |
|---|---|---|---|---|
| 2,627,096 | A | * | 2/1953 | Alessi ................. A44B 9/14 24/710.3 |
| 2,779,985 | A | * | 2/1957 | Turner ................. A47D 15/02 16/93 D |
| 3,136,015 | A | | 6/1964 | Gunderson |
| 3,179,995 | A | * | 4/1965 | Hawk ................. A44B 9/14 24/710.3 |
| 3,225,404 | A | | 12/1965 | Gunderson |
| 3,630,195 | A | * | 12/1971 | Santomieri .......... A61M 25/02 24/336 |
| 3,894,706 | A | * | 7/1975 | Mizusawa ............ F16L 3/237 248/68.1 |
| 4,025,015 | A | * | 5/1977 | Kolic .................. F16L 3/08 248/229.11 |
| 4,295,618 | A | * | 10/1981 | Morota ................ F16L 3/237 248/74.3 |
| 4,691,883 | A | * | 9/1987 | Kurihara .............. F16L 3/13 248/68.1 |
| 4,707,906 | A | * | 11/1987 | Posey .................. F16L 3/223 24/339 |
| 4,840,337 | A | * | 6/1989 | Zaugg ................. F16B 47/003 968/347 |
| 5,382,239 | A | * | 1/1995 | Orr ..................... A61M 25/02 604/177 |
| 5,457,852 | A | * | 10/1995 | Liu ..................... A44C 3/001 24/103 |
| 5,546,938 | A | | 8/1996 | McKenzie |
| 5,800,402 | A | * | 9/1998 | Bierman .............. A61M 25/02 604/174 |
| 5,833,663 | A | | 11/1998 | Bierman et al. |
| 6,804,866 | B2 | * | 10/2004 | Lemke ............ A61M 16/0683 604/174 |
| 7,918,828 | B2 | * | 4/2011 | Lundgaard ............ F16L 3/223 604/179 |
| 9,895,486 | B1 | * | 2/2018 | Carey-Hench .... A61M 16/0875 |
| 9,982,742 | B2 | * | 5/2018 | Loewe ................ B60R 16/0215 |
| 10,285,341 | B2 | | 5/2019 | McCaslin et al. |
| 2002/0157673 | A1 | | 10/2002 | Kessler et al. |
| 2005/0098688 | A1 | * | 5/2005 | Miarka ................ F16L 55/035 248/74.1 |
| 2005/0146676 | A1 | | 7/2005 | Silvestro |
| 2009/0255094 | A1 | * | 10/2009 | Reynolds ............. A45F 5/02 24/3.12 |
| 2010/0115739 | A1 | * | 5/2010 | Mathur ................ A45F 5/02 24/304 |
| 2010/0170066 | A1 | * | 7/2010 | Honeycutt .......... H04R 5/0335 24/390 |
| 2011/0210215 | A1 | * | 9/2011 | Nitsche ................ F16L 3/24 248/74.1 |
| 2011/0286217 | A1 | * | 11/2011 | Martinson ............ B65D 63/00 362/253 |
| 2018/0214672 | A1 | * | 8/2018 | Mulrooney .......... A61M 25/02 |
| 2024/0009086 | A1 | | 1/2024 | Mulrooney |

FOREIGN PATENT DOCUMENTS

| | | |
|---|---|---|
| CN | 204319485 U | 5/2015 |
| EP | 1179307 A2 | 2/2002 |
| EP | 1047469 B1 | 6/2003 |
| EP | 2253350 A1 | 11/2010 |
| EP | 3331597 A1 | 6/2018 |
| JP | 2008220888 A | 9/2008 |
| JP | 2014068716 A | 4/2014 |
| WO | 9844973 A1 | 10/1998 |
| WO | 2005051472 A2 | 6/2005 |
| WO | 2013109835 A1 | 7/2013 |
| WO | 2017021727 A1 | 2/2017 |
| WO | 2020183325 A1 | 9/2020 |

OTHER PUBLICATIONS

Great Britain Search Report for Appl No. GB1513791.9 dtd Jan. 19, 2016, 3 pages.

International Search Report and Written Opinion mailed Jul. 20, 2020, International Application No. PCT/GB2020/050934, 11 pages.

PCT Search Report and Written Opinion for PCT Application No. PCT/GB2016/052381, dated Sep. 26, 2016, 12 pages.

European Patent Office, International Search Report and Written Opinion for International Application No. PCT/GB2020/050934, Jul. 20, 2020, 11 pages.

Great Britain Search Report for Appl No. GB1513797.9 dtd Jan. 19, 2016, 3 pages.

Great Britain Search Report for Appl No. GB1521538.7 dtd Mar. 29, 2016, 5 pages.

Great Britain Search Report for GB Application No. 1513792.0, dated Jan. 4, 2016, 4 pages.

* cited by examiner

GARMENT CLIP

RELATED APPLICATIONS

This application is a continuation of U.S. patent application Ser. No. 15/749,944, filed Feb. 2, 2018, which is a national phase application filed under 35 U.S.C. § 371 of PCT Application No. PCT/GB2016/052381, having an international filing date of Aug. 3, 2016, which claims priority to GB 1513792.0, filed Aug. 4, 2015. Each of these applications is incorporated by reference herein in its entirety.

FIELD

The present invention relates to a garment clip particularly, but not exclusively, for securing a catheter or feeding tube to clothing.

BACKGROUND

Many medical conditions require a patient to be fitted with a catheter, or feeding tube, for an extended period of time. Catheters are most often connected to associated medical equipment that acts in concert with the catheter to deliver substances, collect substances, deliver energy or record information. Catheters are typically inserted into the body of a patient orally, nasally, intracutaneously or via the urethra. As the patient moves, a catheter tends to cause discomfort at the point of entry into the patient's body due to the weight of the part of the catheter located outside of the patient's body. Such discomfort is increased at the point where the catheter interfaces with the patient if the terminal end of the catheter is not restrained in some way, such as if the terminal end of the catheter is disconnected from associated medical equipment.

Catheters routinely require disconnecting from medical equipment while remaining fitted to a patient. The length of catheter remaining fitted to the patient can constitute a tripping or snagging hazard if it is not restrained in some way. The terminal end of the catheter can also act as a source if infection if left exposed and allowed to come into contact with non-sterile surfaces and can cause fluid leakage from the catheter. For example, a catheter inserted into the urethra of a male patient might contain a quantity of urine which, if the catheter was angled towards the floor, would empty.

The problem of loose, or heavy, flexible tubes or cables being difficult to secure on the human body is not unique to the medical field. Conventional earphones or headphones used with a personal media player are connected to the media player by a cable. The cable splits into two at a point typically in the region of a person's chest. The media player might be located adjacent a person's waist or attached to a person's arm. The length of cable between the media player and the person's ears tends to urge the earphones or headphones downwardly and away from the person's ears. This can cause frustration, particularly when the person is active, i.e. running, where earphones can fall out of the person's ears frequently.

The present invention seeks to solve these problems.

SUMMARY

An aspect of the present invention provides a garment clip for attaching a flexible cable or tube to clothing comprising: a body having a clothing facing side and a non-clothing facing side opposite the clothing side, and a clasp on the clothing facing side of the body for attaching the body of the clip to clothing; wherein the non-clothing face side of the body comprises at least one receiving formation, and wherein the at least one receiving formation comprises a resiliently deformable channel for receiving a flexible cable or tube.

Resistance of longitudinal movement of a flexible cable or tube, for example a headphone cable or catheter, is advantageous as movement of the flexible cable or tube can cause discomfort or annoyance to a user if positioned adjacent to the user's face. By resisting movement of the cable or tube, potential longitudinal movement is reduced.

The resiliently deformable channel may comprise two parallel longitudinal channels.

The provision of two resiliently deformable channels of differing dimensions allows the garment clip to restrain catheters or flexible cables of different outer diameter, or having variable outer diameter, using the same garment clip. In particular, catheters having a variable outer diameter along their length may be held in a different position by each resiliently deformable channel. This is advantageous as the patient is free to move around but the terminal end of the catheter is retained in a controlled position. Each resiliently deformable channel may also act on the catheter in different manners. For example, one resiliently deformable channel may act loosely on the catheter whereas the other resiliently deformable channel may be a tighter fit for the catheter and may apply pressure to the catheter. The application of pressure may be useful in closing the catheter tube.

At least one of the two parallel longitudinal channels may comprise a high friction surface, whereby longitudinal movement of the flexible cable or tube is resisted.

The body of the garment clip may be formed from a high durometer thermoplastic elastomer such as Santoprene™. This offers several material properties which are advantageous to the present invention. Such a material is inherently flexible, thus reducing the risk of blunt or persistent trauma to the patient when the garment clip is being worn, by virtue of the compliant nature of the material, and has a high co-efficient of friction. Flexibility is important to enable the channels to deform thus permitting a cable or tube to enter and exit the channel. Friction is important to resist longitudinal movement of the cable or tube relative to the garment clip.

The body of the garment clip may alternatively be formed from a flexible thermoplastic such as polypropylene. The high friction surface in this case may be provided by a liner inserted into at least one of the two parallel longitudinal channels, said liner having a different coefficient of friction than the material of the body. The thickness of the liner may be in the range of 0.5-2 mm. The material of the liner may be for example a thermoplastic elastomer such as Santoprene™. A particularly desirable property of a low durometer grade of this material is that it provides substantial resistance to movement when placed in close contact with other materials even when the compressive forces applied are low. The combination of a more rigid body with a low durometer liner provides the advantage that it allows both compressive forces and surface friction affects to be independently optimised as each property is provided by a separate material.

Some applications may require two cables or tubes to be restrained longitudinally whereas other applications may require one, or no, cables or tubes to be restrained longitudinally. Different embodiments of garment clip can have different configurations of longitudinal channels having a high friction surface and/or low friction surface.

The clasp may be a safety pin.

In some embodiments each of the two parallel longitudinal channels may have different dimensions to the other. In other embodiments each of the two parallel longitudinal channels may have substantially the same dimensions. The width of each of the two parallel longitudinal channels may be in the range of 2-4 mm. The length of each of the two parallel longitudinal channels may be in the range of 5-30 mm. The depth of each of the two parallel longitudinal channels may be in the range of 3-5 mm.

The garment clip may further comprise respective tabs are disposed adjacent to each of the two parallel longitudinal channels, each of said respective tabs being resiliently manoeuvrable to change the configuration of a respective one of the two parallel longitudinal channels wherein when in a first configuration the longitudinal channel has a first dimension and when in a second configuration the longitudinal channel has a second dimension, different to the first such that when in the second configuration a flexible tube or cable is permitted to enter the longitudinal channel and when in the first configuration the flexible tube or cable is restrained laterally within the longitudinal channel.

Provision of a flexible tab permits the body of the garment clip to be manoeuvred so as to change the dimensions of the longitudinal channels. When in a relaxed state a cable or tube held within a longitudinal channel is prevented from being removed laterally from the longitudinal channel. When the tab is flexed, the dimension of the longitudinal channel increases to enable a flexible cable or tube to laterally enter or exit the longitudinal channel.

The respective tabs may be biased in the first configuration.

Aspects of the present invention may be particularly suitable for restraining movement of a catheter or feeding tube. Other aspects of the invention may be particularly suitable for restraining movement of an audio cable or other flexible cable.

BRIEF DESCRIPTION OF THE DRAWINGS

Certain embodiments of the invention will now be described with reference to the following drawings.

DETAILED DESCRIPTION OF THE CERTAIN EMBODIMENTS

Figure 1:
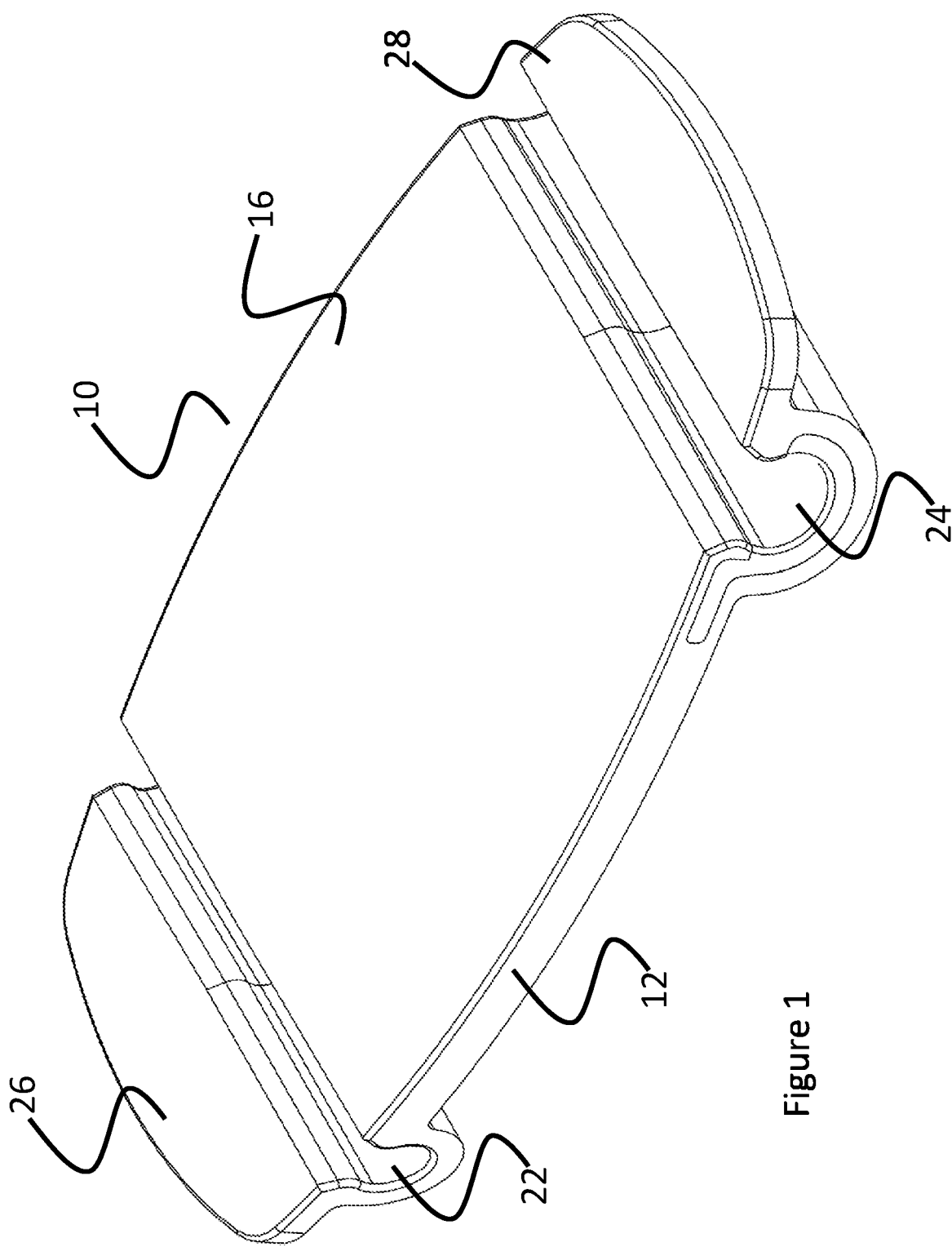
FIG. 1 illustrates a first isometric view of a garment clip according to embodiments of the present invention.
Figure 2:
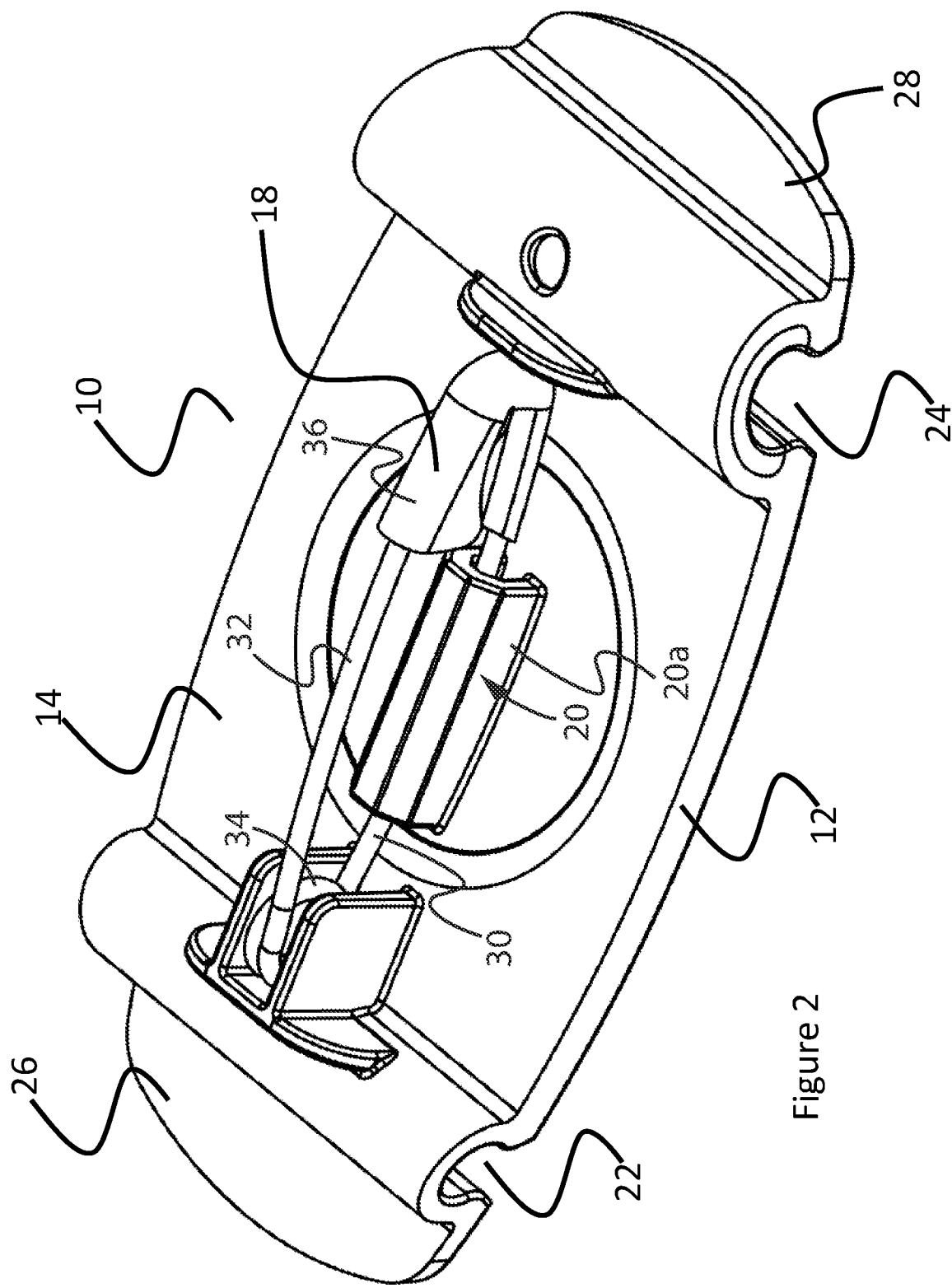
FIG. 2 illustrates a second isometric view of the garment clip of FIG. 1.

A garment clip 10 according to the illustrated embodiment of the invention comprises a body 12 having a clothing facing side 14 and a non-clothing facing side 16. The clothing facing side 14 of the garment clip 10 mounts a clasp 18, for example a conventional safety pin, for securing the garment clip 10 to clothing worn by a person. As shown in FIG. 2, the clasp 18 can comprise a first shaft 30, a second shaft 32, and a spring 34 therebetween. The clasp 18 can comprise a cover 36 opposite the spring 34 along a longitudinal dimension of the clasp 18. The second shaft 32 can comprise a piercing end configured to be received within the cover 36 when the clasp 18 is closed. Accordingly, the second shaft 32 can comprise a piercing member. When the clasp 18 is closed, the second shaft 32 can be substantially parallel to the clothing facing side 14 of the body 12 of the clip 10. The clasp 18, i.e. a standard safety pin in the illustrated embodiment, is retained by the body 12 of the garment clip 10 by a clasp retainer 20 which in the illustrated embodiment comprises a raised protrusion 20a from the body facing side 14 of the body 12. The raised protrusion 20a includes a hole (not shown) running longitudinally therethrough for receiving at least a part of the clasp 18, for example the first shaft 30 as shown in FIG. 2. In the illustrated embodiment the body 12 of the clip 10 is shown as a single piece construction.

At least one deformable channel 22 is formed on the clothing facing side 14 of the body 12 of the garment clip 10. In the illustrated embodiment, two deformable channels 22, 24 are formed in a parallel relationship on the body facing side 14 but it will be appreciated that other embodiments may include just one deformable channel 22, more than two deformable channels 22 or multiple deformable channels which are arranged other than in a parallel relationship.

In the illustrated embodiment, longitudinal channel 22 has a width of 2.6 mm, depth of 3.6 mm and length of 22 mm. A flexible tab 26 is positioned outwardly adjacent to each of the parallel longitudinal channels 22, 24. Each flexible tab 26, 28 is biased in a first position, substantially planar with the body 12.

The body 12 of the garment clip 10 if formed from a flexible thermoplastic elastomer can provide flexibility for a cable or tube to be inserted into each deformable channel 22, 24. The material also provides friction between the cable or tube and garment clip 10 to assist in preventing movement of the cable or tube relative to the garment clip 10. Examples of suitable materials include a high durometer Santoprene™. Alternatively and preferentially the body of the clip is formed from a more rigid thermoplastic such as polypropylene and one or more of the deformable channels 22, 24 may be lined with a different material to the body 12. Such a liner may resist or encourage longitudinal movement of a flexible tube or cable within the deformable channel 22, 24.

In use, a part of a catheter or flexible cable is inserted into a deformable channel 22, 24 by applying a force to the flexible tab 26, 28 so as to deform the body 12 and open the longitudinal channel 22, 24 to permit lateral entry into the longitudinal channel 22, 24 of a flexible cable or tube. The flexible tab 26, 28 is then released to close the longitudinal channel 22, 24 applying compressive holding forces and prevent lateral exit of a flexible cable or tube from the longitudinal channel 22, 24. The flexible cable or tube cannot then easily be removed laterally from the deformable channel 22, 24 until a force is applied to the flexible tab 26, 28 to again open the deformable channel 22, 24.

I claim:

1. A device for securing a catheter to a garment on a patient, the device comprising:
   a garment facing side and a non-garment facing side opposite the garment facing side;
   a body having a garment facing side, a non-garment facing side opposite the garment facing side, and a surface along the non-garment facing side;
   a flexible tab, the tab having a garment facing side, a non-garment facing side opposite the garment facing side, and a surface along the non-garment facing side;
   a resiliently deformable channel disposed at the non-garment facing side of the device and configured to releasably secure the catheter, the channel disposed between the body and the tab and having an opening at the non-garment facing side of the device defined by adjacent edges of the body and tab surfaces and that is substantially planar with the body and tab surfaces,
   wherein the tab is resiliently maneuverable to increase or decrease a cross-sectional dimension of the channel to release or secure the catheter, respectively; and a clasp disposed on the garment facing side of the body and configured to releasably secure the body of the device to the garment, wherein the clasp comprises a piercing member and a cover for receiving the piercing member, the cover being permanently coupled to the body.

2. The device of claim 1, wherein the body includes a high friction material disposed within the channel, and wherein the high friction material is configured to resist longitudinal movement of the catheter along the channel.

3. The device of claim 2, wherein the body comprises a flexible thermoplastic material and the high friction material is a low durometer thermoplastic elastomer.

4. The device of claim 1, wherein the body includes a high durometer thermoplastic elastomer.

5. The device of claim 1, wherein the catheter is a feeding tube.

6. The device of claim 1, wherein the channel is a first channel and the device further comprises a second resiliently deformable channel configured to releasably secure a catheter.

7. The device of claim 1, wherein, when the device is secured to the garment, a longitudinal axis of the piercing member is substantially parallel to the garment facing side of the body.

8. A device for securing a catheter to a garment on a patient, the device comprising:
- a garment facing side and a non-garment facing side opposite the garment facing side;
- a body having a garment facing side, a non-garment facing side opposite the garment facing side, and a surface along the non-garment facing side;
- a flexible tab, the tab having a garment facing side, a non-garment facing side opposite the garment facing side, and a surface along the non-garment facing side;
- a resiliently deformable channel disposed at the non-garment facing side of the device and configured to releasably secure the catheter, the channel having an opening at the non-garment facing side of the device, wherein the opening is defined by adjacent edges of the body and tab surfaces and is substantially planar with the body and tab surfaces and wherein the tab is resiliently maneuverable to change a configuration of the channel, and further wherein
- the channel has a first configuration in which the channel has a first cross-sectional dimension configured to restrain the catheter and
- a second configuration in which the channel has a second cross-sectional dimension different than the first cross-sectional dimension and that allows insertion and removal of the catheter, and
- a clasp disposed on the garment facing side of the body and configured to releasably secure the body of the device to the garment, the clasp comprising a piercing member and a cover configured to be positioned between a portion of the piercing member and the garment when the device is secured to the garment, the cover being permanently coupled to the body, wherein, at least when the device is secured to the garment, a longitudinal axis of the piercing member is substantially parallel to the garment facing side of the body.

9. The device of claim 8, wherein the body includes a high friction material disposed within the channel, and wherein the high friction material is configured to resist longitudinal movement of the catheter along the channel.

10. The device of claim 9, wherein the body comprises a flexible thermoplastic material and the high friction material is a low durometer thermoplastic elastomer.

11. The device of claim 8, wherein the body includes a high durometer thermoplastic elastomer.

12. The device of claim 8, wherein the catheter is a feeding tube.

13. The device of claim 8, wherein the channel is positioned between the tab and the body.

14. The device of claim 8, wherein the channel is a first channel and the device further comprises a second resiliently deformable channel configured to releasably secure a catheter.

* * * * *

UNITED STATES PATENT AND TRADEMARK OFFICE
CERTIFICATE OF CORRECTION

| | | |
|---|---|---|
| PATENT NO. | : 12,220,545 B2 | Page 1 of 1 |
| APPLICATION NO. | : 17/247182 | |
| DATED | : February 11, 2025 | |
| INVENTOR(S) | : Conor Mulrooney | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this
Twenty-fourth Day of June, 2025

Coke Morgan Stewart
*Acting Director of the United States Patent and Trademark Office*